United States Patent [19]

Berger

[11] Patent Number: 5,089,288

[45] Date of Patent: Feb. 18, 1992

[54] METHOD FOR IMPREGNATING TISSUE SAMPLES IN PARAFFIN

[76] Inventor: Hermann J. Berger, Dahlienweg 39c 8400, Regensburg, Fed. Rep. of Germany

[21] Appl. No.: 532,051

[22] Filed: Jun. 1, 1990

[30] Foreign Application Priority Data

Jun. 24, 1989 [DE] Fed. Rep. of Germany ....... 3920819

[51] Int. Cl.$^5$ .............................................. A01G 5/06
[52] U.S. Cl. ................................. 427/4; 427/57; 427/294; 427/416
[58] Field of Search ................. 427/4, 57, 416, 294

[56] References Cited

U.S. PATENT DOCUMENTS

| | | | |
|---|---|---|---|
| 3,961,097 | 6/1976 | Gravlee, Jr. ........................ | 427/2 |
| 4,497,792 | 2/1985 | Gindler ................................ | 427/4 |
| 4,656,047 | 4/1987 | Kok et al. ............................. | 427/4 |
| 4,839,194 | 6/1989 | Malluche et al. ..................... | 427/4 |
| 4,865,871 | 9/1989 | Livesey et al. ....................... | 427/4 |
| 4,891,239 | 1/1990 | Dudley et al. ........................ | 427/4 |

FOREIGN PATENT DOCUMENTS 2065912 7/1981 United Kingdom .

Primary Examiner—Michael Lusignan
Assistant Examiner—Diana Dudash

[57] ABSTRACT

A method of impregnating a tissue sample with paraffin in which, in a treatment vessel, a tissue sample, which has been fixed with isopropyl alcohol, is maintained under vacuum and simultaneously the molten paraffin and tissue sample are subjected to ultrasonic vibration effective to remove the isopropyl alcohol from the tissue sample and to impregnate the tissue sample with the paraffin.

11 Claims, 1 Drawing Sheet

METHOD FOR IMPREGNATING TISSUE SAMPLES IN PARAFFIN

FIELD OF THE INVENTION

The invention relates to a method for impregnating or soaking human, animal or plant tissue samples with paraffin.

BACKGROUND OF THE INVENTION

Methods of impregnating tissue samples with solid paraffin are known, are used in industry and, in particular, also in medicine in order to embed tissue samples, after their fixation, dewatering and soaking with paraffin, in paraffin blocks and to prepare these in this manner for a subsequent microscopic examination (histology). The thinnest sections or slices can then be obtained from the tissue samples embedded in paraffin blocks which sections can be examined under a microscope. The term "tissue samples" is to be understood in the sense of the invention as tissue samples in general, namely, human, animal or plant tissue samples.

The tissue samples in a known method (German OS No. 30 47 417), which tissue samples are fixed with a suitable fixing medium (for example, isopropyl alcohol) and are subsequently dewatered through isopropyl alcohol (isopropanol), are impregnated with paraffin without using an intermediate medium (for example xylol), and are thereafter also embedded in paraffin. The impregnating in paraffin takes place at ambient pressure and at a temperature slightly higher than the melting point of the paraffin. In the case of the usually utilized paraffins, the melting point lies approximately between 50° C. and 58° C. To soak the tissue samples, they are dipped into or under the liquid paraffin, namely, are surrounded by the liquid paraffin. The replacement of the isopropyl alcohol contained in the tissue of the tissue samples with paraffin is effected by dissolving the isopropyl alcohol in paraffin such that, during the course of the treating or impregnating time, the concentration of the paraffin in the "isopropyl alcohol-paraffin solution" increases also in the tissue of the tissue samples. With this known method it is not possible, or is possible only over a very long impregnating time, to completely replace the isopropyl alcohol in the tissue of the tissue samples with paraffin or to replace it with paraffin to the degree necessary to achieve adequate quality of the embedded paraffin and thus also necessary for the quality of the tissue sections.

In addition to long impregnating times, the known methods have, among others, also the disadvantage that a considerable contamination of the paraffin with isopropyl alcohol occurs, which means either that additional expensive measures are required for cleaning the paraffin or, on the other hand (because of the necessary paraffin replacement), an increased consumption of paraffin.

The purpose of the invention is to provide a method for impregnating or soaking tissue samples with paraffin, which method avoids the aformentioned disadvantages and, among other advantages, enables a quick and economical impregnating and also embedding of tissue samples in paraffin.

To attain this purpose, a method according to the invention includes the soaking of the tissue sample in a closed, evacuated working chamber under the influence of ultrasound (ultrasonic vibrations) on the tissue sample and on the liquid paraffin surrounding the tissue sample. A vacuum is provided in the working chamber such that under the pressure existing in the working chamber, the boiling point of the isopropyl alcohol is equal to or is below the operating temperature in the working chamber. The operating temperature suitably lies in the range between about 52° C. and about 60° C.

The method of the invention has, amongst others, the advantage, compared with known methods, that significantly shorter impregnating times can be achieved, that is, impregnating times on the order of magnitude of 20 to 30 minutes, for tissue samples of lesser thickness, so that "high-speed paraffin sections" can be obtained utilizing the method of the invention, which sections, for example, during an on-going surgery permit a microscopic examination and diagnosis of a tissue sample and thus, due to this examination, enables suitable surgical steps to be taken during the surgery. The method of the invention has furthermore the advantage that contamination of the paraffin with isopropyl alcohol and thus replacement of paraffin are minimized or avoided, so that the inventive method is also very economical.

The method of the invention achieves also a reduction of the operating temperature, below the melting temperature of paraffin at atmospheric pressure, by applying a vacuum to the working chamber. Thus, it is possible to soak tissue samples with paraffin at very low temperatures, so that also temperature-volatile substances are maintained in the tissue samples and can be identified/traced during subsequent examinations. Their identification is not possible in the known methods.

Aside from a quick, optimum soaking, the method of the invention opens up also new possibilities in the diagnostics field. For example, the method of the invention maintains the operating temperature, the ultrasound treatment and the reduced pressure in the working chamber, which pressure lies, for example, in the order of magnitude of 100 mbar, constant over the entire impregnating time.

The use of isopropyl alcohol also has the particular advantage that whereas this alcohol does escape from the respective tissue sample in the evacuated working area through boiling, said escape takes place so slowly that the paraffin has enough time to penetrate into the tissue sample, and in this way an optimal impregnation of the tissue sample with paraffin is achieved, in particular even in tissue samples—e.g. fat tissues—where impregnation with paraffin calls for a particularly careful mode of operation. The optimal impregnation is further supported in such a way that during impregnation or during the period of treatment of the tissue sample the pressure is increased at least once above the reduced pressure, and then again decreased to the reduced pressure. In so doing the pressure is preferably increased to atmospheric pressure. The total time during which an increased pressure is present is preferably 30–40% of the duration of treatment. During the change in pressure the action of ultrasound on the tissue is preferably maintained.

BRIEF DESCRIPTION OF THE DRAWING

The invention will be discussed in detail hereinafter with references to FIG. 1 which, in a schematic illustration and in cross section, shows an impregnating chamber or rather a working receptacle.

DETAILED DESCRIPTION

Figure 1:
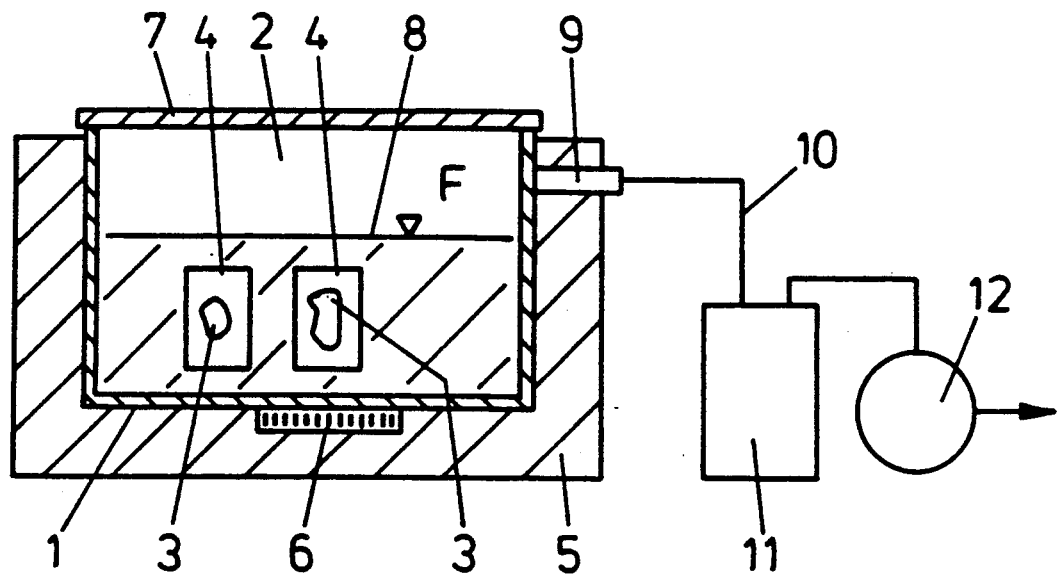
Figure 1:
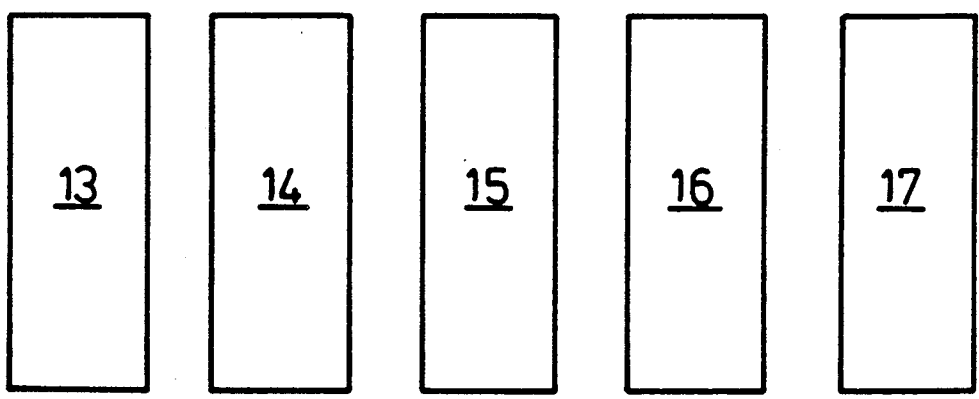

FIG. 1 illustrates the working receptacle 1, which is designed as a trough or pot or other type of vessel having a closed bottom and a closed peripheral wall and which, with its inner chamber 2, forms the treating or impregnating chamber for tissue samples 3, in which each tissue sample 3 is arranged in a cassette 4 commonly used during impregnating or embedding of tissue samples in paraffin. Each cassette 4 is designed as a box-like container having a closable lid, which lid is a screen-like member, and a screen-like bottom so that the treating medium introduced into the inner chamber 2 of the working receptacle 1 can contact and treat the tissue sample 3 in the cassette 4 through the screen-like bottom and the screen-like lid of each cassette 4.

The working receptacle is at least partly surrounded by means 5 enabling heating of the inner chamber 2 such that the temperature of the inner chamber 2 and thus also of a treating medium introduced into the inner chamber 2 is maintained as constant as possible at a pregiven or set temperature. The means 5 include, for example, a water bath, which is heated with a suitable, regulatable heating device, or more preferably, a temperature-controllable chamber, namely a chamber through which air flows with a controlled temperature, thus also permitting cooling of the inner chamber 2 and the treating medium.

At least one ultrasound generator 6 is provided on the working receptacle 1, which ultrasound generator 6 is designed as an electro-mechanical converter and is controlled by an electric generator (not illustrated) having a frequency within the ultrasound range, namely, having a frequency, for example, in the range between 35 and 50 KHz. The generator 6 applies, in particular to the treating medium introduced into the inner chamber 2 and primarily also to the tissue samples 3 in the chamber, a suitable ultrasound energy. The output of the ultrasound generator 6 lies on the order of magnitude of 100 Watts or several 100 Watts, depending on the size of the working receptacle 1, that is, for example, between 120 Watts in the case of a small working receptacle and 1.2 Kilowatts in the case of a larger working receptacle.

The working receptacle 1 can be closed off airtight and vacuum-tight by a lid 7 at the usually open upper side. Just like the working receptacle 1, this lid 7 can also have many different designs, which are actually known to one of skill in the art.

The respective treating medium is introduced into the inner chamber up to a level F of fill such that an air space remains in the inner chamber 2 above the upper surface 8 and the lid 7. A connection 9 is provided in the region of the air space at a sufficient distance from the level 8. The connection 9 is connected or can be connected continuously through a pipeline 10 to a washing basin or filter 11. The output of the filter 11 is connected to a vacuum pump 12.

The working receptacle 1, in the illustrated embodiment, is the reaction receptacle of a single-chamber embedder (single-chamber system), that is, the entire pretreatment of the tissue samples 3 and their soaking in paraffin occurs exclusively in the working receptacle 1. Tanks 13 to 17 are for this purpose associated with the working receptacle, in which tanks the various treating media are kept ready, each at a respectively pregiven temperature. The tank 13 contains a fixing liquid (for example, isopropyl alcohol) to fix the tissue samples 3 (for example, at a temperature of 40° C.), the tank 14 contains 70% isopropyl alcohol, the tanks 15 and 16 contain each 100% isopropyl alcohol and the tank 17 contains liquid paraffin, with the tanks 14 to 17 being maintained approximately at the same temperature, namely, at a temperature of, for example, approximately 58° C., which in this design corresponds with the operating temperature and is necessary to maintain the liquid state of the paraffin in the tank 17. The temperature of the tanks 14 to 17 is in every case significantly lower than the boiling point (approximately 82.8° C.) of the isopropyl alcohol (isopropanol) at normal atmospheric pressure.

A suitable connecting pipeline system (not illustrated) and a pump and/or valve system makes it possible to move the individual treating media, which are ready in the tanks 13 to 17, into the inner chamber 2 of the working receptacle and to return the media from the inner chamber 2 again into the respective tanks 13 to 17.

In order to soak the tissue samples 3 with the paraffin from the tank 17, a fixation and dewatering of the tissue samples is done first, after which the impregating or soaking with paraffin can be carried out without treatment with an intermediate medium. The following method steps are carried out individually after the cassette 4 with the tissue samples 3 has been moved into the inner chamber 2 and after the inner chamber has been closed off by the lid 7.

First, the fixing agent, which, for example, is also isopropyl alcohol or, alternatively, another suitable fixing agent, is moved from the tank 13 into the inner chamber 2 up to the pregiven fill level F. The temperature of the fixing agent is increased to the operating temperature through the ultrasound energy of the ultrasound generator 6, which operating temperature lies, for example, on the order of magnitude of 58° C. After the fixing of the tissue samples 3, the fixing agent is returned into the tank 13.

The inner chamber 2 is thereafter filled with isopropyl alcohol from the tank 14, again to the fill level F. This isopropyl alcohol has already the operating temperature because of the temperature at which the tanks 14 to 17 are held. To facilitate the partial dewatering carried out with the filling of 70% isopropyl alcohol, again the treating medium and the tissue samples 3 are subjected to ultrasonic vibrations. After the partial dewatering of the tissue samples has been achieved and the fixing agent has also been washed out, the 70% isopropyl alcohol is returned into the tank 14.

A further dewatering and degreasing of the tissue samples 3 is then done with the 100% isopropyl alcohol from the tank 15, again during application of ultrasound. After this filling has been returned into the tank 15, the final dewatering and degreasing of the tissue samples 3 finally takes place by suitably filling the inner chamber 2 with the isopropyl alcohol from the tank 16, also during application of ultrasound vibration.

After this last filling of isopropyl alcohol is returned into the tank 16, the soaking of the tissue samples 3 with the paraffin is started. Liquid paraffin from the tank 17 is for this purpose moved into the inner chamber 2 up to the fill level F. With the working receptacle closed off vacuum-tight by the lid 7, the pressure inside of the inner chamber 2 is then lowered by means of the vacuum pump 12 until it lies approximately at an order of magnitude of 100 mbar, thus a vacuum of a high quality is achieved in the inner chamber 2 and is maintained over the time needed to soak the tissue samples, during which a simultaneous treatment of the liquid paraffin and of the tissue samples 3 with ultrasound energy occurs. By lowering the pressure in the inner chamber 2 of the working receptacle 1, which lowering is done preferably as abruptly as possible, the boiling point of the isopropyl alcohol at the operating temperature is exceeded, so that the isopropyl alcohol still remaining in the tissue samples and having a boiling temperature at normal pressure of approximately 82.8° C. evaporates, exits from the tissue samples through the liquid paraffin enclosing the tissue samples 3 and is discharged through the connection 9. The space set free by the evaporation of the isopropyl alcohol from the tissue samples 3 is immediately occupied with liquid paraffin without the isopropyl alcohol dissolving in the paraffin. This method makes it possible to carry out in a very short period of time a paraffin embedding or soaking of tissue samples. In the case of very thin tissue samples having a thickness of approximately 2 mm, impregnating times of only 20 to 30 minutes can be achieved. Also in the case of tissue samples of greater thickness, for example, a thickness of between 3–4 mm, impregnating times can be achieved which lie in the range of between 1 and 1½ hours.

The paraffin impregnation of tissue samples possible with the described method meets the highest quality demands in spite of the extreme shortening of the impregnating times compared with common methods. In particular, it is also possible with the aforedescribed method to completely ventilate air-containing tissues, for example lung tissue, thus to impregnate them in paraffin without air pockets, so that also these tissues can provide optimum sections for microscopic examinations (histology).

The short impregnating times attainable with the method of the invention can only be attained due to the evaporation of the isopropyl alcohol in combination with the ultrasound treatment which causes a temporary (momentary) underpressure to be created in the tissue samples, which underpressure aids the penetration of the relatively large paraffin molecule into the tissue. It is hereby also decisive that through the ultrasound loading, the evaporation of the isopropyl alcohol starts immediately when, during the rather abrupt lowering of the pressure in the inner chamber 2, the boiling point of the isopropyl alcohol is reached.

The operating temperature, the ultrasound loading and the vacuum are maintained over the entire required impregnating time in each case.

A further important advantage of the aforedescribed method is that the isopropyl alcohol does not penetrate into the paraffin, so that, after soaking the tissue samples 3, the paraffin can be discharged from the inner chamber 2 again into the tank 17. In contrast to known methods, no further tank is thus needed for receiving the paraffin contaminated by isopropyl alcohol and also no special measures for paraffin recovery are needed. Only the paraffin consumed during the paraffin impregnation of the tissue samples 3 must be replaced in the tank 17. Thus, the described method is also distinguished by being very economical.

After the tissue samples 3 have been soaked in paraffin, they are cast into a paraffin block in the usual manner.

Of course, the aforedescribed method is not only applicable in a single-chamber system, but also in a multi-chamber system in which several work stations, each with one chamber, are provided for the individual operations and the tissue samples 3 or rather the cassettes 4 are forwarded from work station to work station. The tissue samples 3 are then soaked with paraffin in the aforedescribed manner at one of the work stations following a preceding treatment of the tissue samples 3 with isopropyl alcohol.

What is claimed is:

1. In a method for impregnating a tissue sample with paraffin, the improvement comprising:
    fixing the tissue sample with a fixing agent;
    dewatering the tissue sample by using alcohol;
    treating the tissue sample in isopropyl-alcohol; and
    soaking the tissue sample in liquid paraffin by the tissue sample being placed into the paraffin in a working chamber at a pregiven operating temperature, the operating temperature being in the range of about 52° to 60° C. in order to keep the paraffin in a liquid state and therefore lower than the boiling temperature of isopropyl alcohol at a normal atmospheric pressure;
    the tissue sample being soaked in a closed, evacuated working chamber under the influence of ultrasound on the tissue sample and on the liquid paraffin enclosing the tissue sample; and the vacuum in the working chamber being chosen such that the boiling point of the isopropyl alcohol equals the operating temperature at the pressure existing in the working chamber.

2. The method of claim 1 wherein the ultrasound treatment is maintained constant over the entire time needed for impregnating the tissue sample.

3. The method of claim 1 wherein the operating temperature and/or the pressure existing in the working chamber is maintained constant over the entire impregnating time needed for impregnating.

4. The method of claim 1 wherein for a tissue sample of 2 mm thickness an impregnating time of approximately 20 to 30 minutes is chosen.

5. The method of claim 1 wherein for a tissue sample of approximately 3 mm to 4 mm thickness an impregnating time of 1–1.5 hours is chosen.

6. The method of claim 1 wherein the ultrasound has a frequency in the range of between about 35 kHz and about 50 kHz.

7. The method of claim 1 wherein the ultrasound has a power in the range of between about 120 Watts and about 1200 Watts.

8. The method of claim 1 wherein the pressure in the working chamber is about 100 mbar.

9. The method of claim 1, characterized in that during impregnation of during the period of treatment of the tissue sample (3) the pressure in the working area (2) is increased at least once above the reduced pressure and then decreased again to the reduced pressure, the total time of treatment of the tissue sample with the increased pressure amounting to about 30–40% of the duration of treatment.

10. The method of claim 9 wherein the pressure is increased to atmospheric pressure.

11. The method of claim 9 wherein the change in pressure takes place while maintaining the treatment of the tissue sample by ultrasound.

* * * * *

UNITED STATES PATENT AND TRADEMARK OFFICE
CERTIFICATE OF CORRECTION

PATENT NO. : 5,089,288

DATED : February 18, 1992

INVENTOR(S) : Hermann J. Berger

It is certified that error appears in the above-identified patent and that said Letters Patent is hereby corrected as shown below:

COLUMN 6
    Claim 9, line 2, change "of" (first instance) to --or--; line 3, delete "(3)" and "(2)".

Signed and Sealed this

Fourth Day of May, 1993

Attest:

MICHAEL K. KIRK

Attesting Officer      Acting Commissioner of Patents and Trademarks